United States Patent [19]

Epstein

[11] 4,118,417

[45] Oct. 3, 1978

[54] PROCESS FOR RESOLVING CIS-1-SUBSTITUTED PHENYL-1,2-CYCLOPROPANEDICAR-BOXYLIC ACIDS

[75] Inventor: Joseph William Epstein, Monroe, N.Y.

[73] Assignee: American Cyanamid Company, Stamford, Conn.

[21] Appl. No.: 809,340

[22] Filed: Jun. 23, 1977

[51] Int. Cl.$^2$ ...................... C07C 63/00; C07D 207/00
[52] U.S. Cl. .................................. 562/401; 260/313.1
[58] Field of Search ........... 260/515 A, 515 P, 518 R, 260/520

[56] References Cited

PUBLICATIONS

Eliel "Stereochemistry of Carbon Compounds" (1962) pp. 49–64.

*Primary Examiner*—A. Siegel
*Attorney, Agent, or Firm*—Claude J. Caroli

[57] ABSTRACT

A method for resolving racemic substituted cyclopropanedicarboxylic acids which are useful as intermediates for the preparation of substituted phenyl azabicyclohexanes which possess anxyolitic and analgesic activity.

3 Claims, No Drawings

PROCESS FOR RESOLVING CIS-1-SUBSTITUTED PHENYL-1,2-CYCLOPROPANEDICARBOXYLIC ACIDS

BACKGROUND OF THE INVENTION

Applicant is not aware of any prior art references which, in his judgment as one skilled in the art, would anticipate or render obvious the novel process of the instant invention; however, for the purpose of fully developing the background of the invention and establishing the state of the requisite art, the following reference is set forth: U.S. Pat. No. 3,892,772.

SUMMARY OF THE INVENTION

This invention is concerned with a process for resolving racemic substituted cyclopropanedicarboxylic acids of the formula (I):

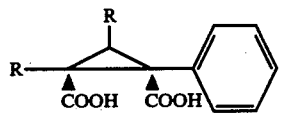

wherein R is selected from the group consisting of hydrogen and $C_1$–$C_6$ alkyl; and the phenyl moiety is unsubstituted, mono-or di-substituted from the group consisting of hydrogen, halogen, $C_1$–$C_6$ alkyl, $C_1$–$C_6$ alkoxy, trifluoromethyl, nitro, amino, acetamido and hydroxy; into their (+) and (−) isomers.

DESCRIPTION OF THE INVENTION

The instant resolution procedure provides the above shown optically active intermediates which are used in making an optically active compound of the formula:

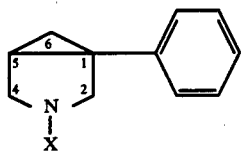

wherein the phenyl moiety is unsubstituted or mono- or di-substituted from the group consisting of halogen, straight chain $C_1$–$C_6$ alkyl, $C_1$–$C_6$ alkoxy, trifluoromethyl, nitro, amino, acetamido and hydroxy; X is selected from the group consisting of hydrogen, straight chain $C_1$–$C_8$ alkyl, and a moiety of the formula $C_nH_{2n}R_1$, wherein n is an integer from 1 to 3 and $R_1$ is selected from the group consisting of phenyl and p-fluorobenzoyl; the racemic mixture thereof; the mirror image thereof; and the non-toxic pharmaceutically acceptable salts thereof. These optically active azabicyclohexane compounds are useful as anxyolitic and analgesic agents. An azabicyclohexane of particular interest is 1-(p-tolyl)-3-azabicyclo[3.1.0]hexane.

The resolution process consists of reacting a racemic mixture of a substituted cyclopropanedicarboxylic acid of formula (I) with either (+) or (−)-α-(1-naphthyl)-ethylamine in an organic solvent such as tetrahydrofuran. The resulting solid is collected, slurried in water, basified, extracted with ether to remove unreacted amine, and then the aqueous solution is acidified to produce crystals of the (+) or (−) isomer, depending upon which isomer of α-(1-naphthyl)-ethylamine has been used in the reaction.

DETAILED DESCRIPTION OF THE INVENTION

EXAMPLE 1

Resolution of (±)-cis-1-p-tolyl-1,2-cyclopropanedicarboxylic acid

A 76.2 g portion of racemic (±)-cis-1-p-tolyl-1,2-cyclopropanedicarboxylic acid and 161.6 g of brucine tetrahydrate in 1.5 liters of 3A alcohol is boiled until solution is complete and then allowed to stand at room temperature. The solid is collected (the mother liquor is saved) and recrystallized from one liter of 3A alcohol. These crystals are suspended in water and the slurry is made strongly basic with 5N sodium hydroxide. The mixture is filtered and the filtrate is made acidic with an excess of 12N hydrochloric acid and the resulting crystals are collected and air dried giving 16.3 g of the (−) isomer, $[\alpha]_D^{25} = -189°$ (C = 1.00 $CH_3OH$).

The mother liquor from the initial reaction gives a second crop which is removed by filtration. This filtrate is evaporated giving 118 g of semicrystalline solid which is treated as described above with base and then acid giving 34.0 g of the (+) isomer $[\alpha]_D^{25} = +132°$.

A solution of 31.6 g of the above diacid [α = +132°] in 100 ml of tetrahydrofuran is poured into a solution of 24.6 g of (−)-α-(1-naphthyl)-ethylamine ($[\alpha]_D^{25} = -60°$) in 100 ml of tetrahydrofuran to give a solution which upon scratching gives colorless crystals. The colorless crystals are collected by filtration and a 30 g portion of these crystals are slurried in 100 ml of water and basified with 40 ml of 5N sodium hydroxide. This mixture is extracted twice with ether. The aqueous portion is made acidic with 15 ml of 12N hydrochloric acid, cooled and filtered giving 15.58 g of the (+) isomer as colorless crystals, $[\alpha]_D^{25} = +193°$.

EXAMPLE 2

Preparation of (+)-1-(p-Tolyl)-3-azabicyclo[3.1.0]hexane hydrochloride

A solution of 94.8 g of racemic-1-(p-tolyl)-1,2-cyclopropanedicarboxylic acid and 73.8 g of (−)-α-(1-naphthyl)-ethylamine in 300 ml of tetrahydrofuran is diluted with 300 ml of ethyl ether and is allowed to stand at room temperature until crystallization is complete. The mixture is filtered and the crystals which are collected are washed with cold tetrahydrofuran to give 49.5 g of a salt comprised of one molar equivalent of (+)-1-(p-tolyl)-1,2-cyclopropanedicarboxylic acid and one molar equivalent of (−)-α-(1-naphthyl)-ethylamine. The salt is shaken with sodium hydroxide solution and ether. The aqueous phase is acidified with 12N hydrochloric acid and the product is collected by filtration to give 26.0 g of (+)-1-(p-tolyl)-1,2-cyclopropanedicarboxylic acid as colorless crystals, $[\alpha]_D^{CH_3OH} = +192°$.

A 15.0 g portion of (+)-1-(p-tolyl)-1,2-cyclopropanedicarboxylic acid, 6.6 g of urea and 500 ml of xylene is refluxed and stirred for 5 hours. The reaction mixture is then filtered hot and the filtrate is evaporated under reduced pressure to give (+)-1-(p-tolyl)-1,2-cyclopropanedicarboximide as colorless crystals, m.p. 148°–155° C.

A 14 g portion of the above product is mixed with 420 ml of benzene and 112 ml of sodium bis(2-methoxyethoxy)aluminum hydride (70% benzene solution) is added over a 15 minute period with stirring. After refluxing for 1½ hours the mixture is cooled and 160 ml of 10N sodium hydroxide is added. The organic layer is dried over sodium sulfate, filtered and evaporated to an oil. The oil is dissolved in ether and hydrogen chloride gas is bubbled in. The solid which form is recrystallized from acetonitrile giving (+)-1-(p-tolyl)-3-azabicyclo[3.1.0]hexane hydrochloride as colorless crystals, m.p. 208°–210.5° C., $[\alpha]_D^{CH_3OH} = +64.5°$.

In the above manner, (−)-1-(p-tolyl)-1,2-cyclopropanedicarboxylic acid is converted to (−)-1-(p-tolyl)-1,2-cyclopropanedicarboximide, m.p. 145°–148° C., $[\alpha]_D^{CH_3OH} = -74°$ and this is then reduced to give (−)-1-(p-tolyl)-3-azabicyclo [3.1.0]hexane hydrochloride as colorless crystals, m.p. 204°–207° C., $[\alpha]_D^{CH_3OH} = -64°$.

I claim:

1. A method for resolving a compound of the formula:

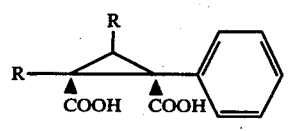

wherein R is selected from the group consisting of hydrogen and $C_1$–$C_6$ alkyl; and the phenyl moiety is unsubstituted, mono- or di-substituted from the group consisting of hydrogen, halogen, $C_1$–$C_6$ alkyl, $C_1$–$C_6$ alkoxy, trifluoromethyl, nitro, amino, acetamido and hydroxy; into their (+) and (−) isomers which comprises reacting said compound with either (+) or (−)-α-(1-naphthyl)-ethylamine, in tetrahydrofuran, to produce a solid; collecting said solid, slurring in water, basifying, extracting with ether, and acidifying.

2. A method according to claim 1, wherein said compound is (+)-cis-1-p-tolyl-1,2-cyclopropanedicarboxylic acid.

3. A method according to claim 1, wherein said compound is (−)-cis-1-p-tolyl-1,2-cyclopropanedicarboxylic acid.

* * * * *